United States Patent
Carter

(10) Patent No.: US 10,406,055 B2
(45) Date of Patent: Sep. 10, 2019

(54) DEVICE AND METHOD OF STABILIZING PATIENT'S LIMB

(71) Applicant: Arthrex, Inc., Naples, FL (US)

(72) Inventor: Thomas R. Carter, Phoenix, AZ (US)

(73) Assignee: ARTHREX, INC., Naples, FL (US)

(*) Notice: Subject to any disclaimer, the term of this patent is extended or adjusted under 35 U.S.C. 154(b) by 370 days.

(21) Appl. No.: 14/659,242

(22) Filed: Mar. 16, 2015

(65) Prior Publication Data

US 2016/0270995 A1    Sep. 22, 2016

(51) Int. Cl.
*A61G 13/00* (2006.01)
*A61G 13/10* (2006.01)
*A61F 5/37* (2006.01)
*A61G 13/12* (2006.01)

(52) U.S. Cl.
CPC ............... *A61G 13/10* (2013.01); *A61F 5/37* (2013.01); *A61G 13/1245* (2013.01); *A61F 5/3769* (2013.01); *A61G 13/101* (2013.01); *A61G 2200/32* (2013.01); *A61G 2210/10* (2013.01)

(58) Field of Classification Search
CPC ........ A61F 5/37; A61F 5/3761; A61F 5/3769; A61F 5/3792; A61G 13/10; A61G 13/12; A61G 13/1235; A61G 13/1245; A61G 13/1255; A61G 13/1285; A61G 13/128; A61G 13/129; A61G 13/101; A61G 13/1205–1255; A61G 2200/32; A61G 7/065; A61G 7/075; A61G 7/0755; A61G 7/1082; A61G 7/1096; A61G 7/109; A61G 2210/10

USPC ........ 128/845, 846, 878, 875, 877, 881, 882
See application file for complete search history.

(56) References Cited

U.S. PATENT DOCUMENTS

| | | | | |
|---|---|---|---|---|
| 1,706,634 A * | 3/1929 | Seils | ..................... | B60N 2/4666 128/877 |
| 2,535,559 A * | 12/1950 | Wolf | ...................... | A61G 13/12 5/621 |
| 2,678,857 A * | 5/1954 | Hans | ..................... | A61G 13/12 5/621 |
| 3,251,360 A * | 5/1966 | Melges | .................. | A61B 46/30 128/853 |
| 3,389,702 A * | 6/1968 | Kennedy | ................ | A61B 17/42 5/631 |
| 4,526,355 A * | 7/1985 | Moore | ............... | A61G 13/0063 5/624 |

(Continued)

FOREIGN PATENT DOCUMENTS

FR    2732213 A1    10/1996

OTHER PUBLICATIONS

International Preliminary Report on Patentability for International application No. PCT/US2016/020401 dated Sep. 28, 2017.

*Primary Examiner* — Keri J Nelson
*Assistant Examiner* — Adam Baker
(74) *Attorney, Agent, or Firm* — Carlson, Gaskey & Olds

(57) ABSTRACT

Devices and methods for positioning a patient's leg during a leg or knee operation by employing a novel surgical leg positioning device. The device has a low profile so that it can remain under sterile surgical drapes during an operation, and prevents the leg from moving out or up. Large, easy to access, buttons are provided to allow the surgical leg positioning device to be manipulated while under sterile surgical drapes so that it may be moved when no longer needed.

12 Claims, 8 Drawing Sheets

(56) References Cited

U.S. PATENT DOCUMENTS

| | | | | |
|---|---|---|---|---|
| 4,547,092 | A | * | 10/1985 | Vetter .................. A61G 7/0503 248/229.11 |
| 4,549,540 | A | * | 10/1985 | Caspari ................ A61F 5/3761 128/882 |
| 4,996,977 | A | * | 3/1991 | Tiedeken .............. A61F 5/3761 128/878 |
| 5,390,383 | A | * | 2/1995 | Carn ...................... A61G 13/12 128/877 |
| 6,622,324 | B2 | * | 9/2003 | VanSteenburg ........ A61G 13/04 128/845 |
| 6,820,621 | B2 | * | 11/2004 | DeMayo ................ A61G 13/12 128/845 |
| 6,941,951 | B2 | * | 9/2005 | Hubert ............... A61G 13/0054 128/845 |
| 8,099,808 | B1 | * | 1/2012 | McKeon ........... A61G 13/0063 5/621 |
| 8,689,793 | B2 | * | 4/2014 | Kring .................. A61B 17/132 128/845 |
| 2010/0263129 | A1 | | 10/2010 | Aboujaoude |
| 2011/0114803 | A1 | * | 5/2011 | Lee ...................... A61G 13/101 248/70 |

\* cited by examiner

DEVICE AND METHOD OF STABILIZING PATIENT'S LIMB

FIELD OF THE INVENTION

The present invention relates to the field of surgery and, more particularly, to limb positioning and stabilizing devices.

BACKGROUND OF THE INVENTION

Knee surgery is extremely common. To operate, the knee must be positioned in a particular manner, and able to be moved if or when the surgeon needs it to move. Depending on the type of knee surgery, the placement of the knee and leg differs and positioning of the knee in a predetermined position is important.

Versatile and less cumbersome positioners that allow for a surgeon to move them without removing the sterile drapes are needed. Also needed are adjustable positioning and stabilizing devices for attachment to surgical tables for positioning and stabilizing a patient's limb, as well as improved leg stabilizers that allow movement in three distinct axes of rotations and/or planes. Methods of manipulating a surgical limb positioner or stabilizer during the surgery and while the positioner or stabilizer is completely under surgical drapes are also needed.

BRIEF SUMMARY OF THE INVENTION

The present invention provides devices for positioning and stabilizing a patient's leg during a leg or knee operation, and methods for using and manipulating the devices.

The present invention provides a surgical leg positioning device that can be affixed to a rail on an operating table and be configured to move in three different planes, allowing for a great degree of freedom for positioning a patient's leg for surgery. The surgical leg positioning device has a low profile so that it may be disposed underneath sterile surgical drapes during an operation, and may be moved out of the way as needed while still under the sterile drapes. The surgical leg positioning device can be configured to move in three planes of motion: rotating, in/out, and up/down.

The present invention also provides methods for manipulating the surgical leg positioning device that may be moved in three different planes, before and during an operation.

These and other features and advantages of the invention will be more apparent from the following detailed description that is provided in connection with the accompanying drawings and illustrated exemplary embodiments of the invention.

DETAILED DESCRIPTION OF THE INVENTION

Figure 1:
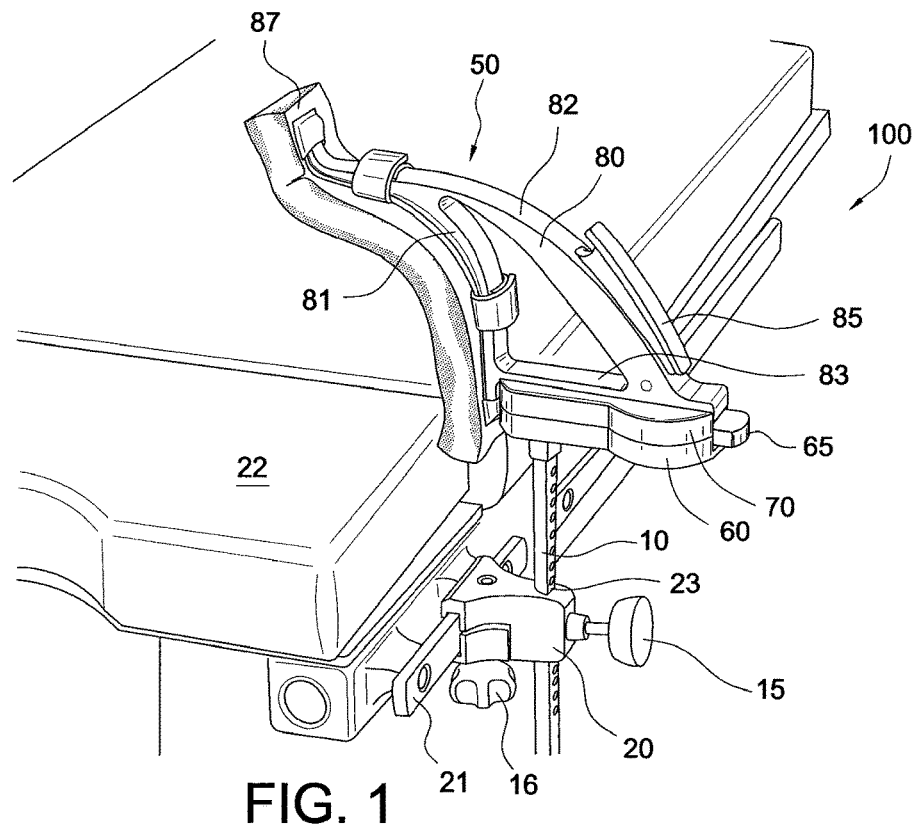
FIG. 1 illustrates an exemplary embodiment of a surgical leg positioning device of the present invention, mounted to an operating table.

The present invention provides devices for positioning and stabilizing a patient's leg during a leg or knee operation with a leg positioning or stabilizing device, and methods for using and manipulating the leg positioning or stabilizing device during surgeries such as knee arthroscopic surgeries.

As detailed below, the surgical leg positioning device of the present invention is a stabilizing device in the form of a lateral post that moves in three planes to easily place in the proper position to the patient, and pivot out of the way when not in use. This allows it to be easily placed in the proper position to the patient and also pivot out of the way when not in use. The unique over-the-top sweeping design of the leg positioning device prevents the patient's leg from moving over the post when valgus stress or a figure four is applied. The ergonomic, oversized buttons are easily located under the drape. There are also disposable pads for patient's comfort that are easy to put on and take off. The leg positioning device attaches easily to an OR bed with its custom Clark rail adapter.

The surgical leg positioning device can be affixed to a standard rail (a Clark rail) on an operating table and be configured to move in three different planes, allowing for a great degree of freedom for positioning a patient's leg for surgery. The surgical leg positioning device has a compact, low profile so that it may be disposed underneath sterile surgical drapes during an operation and may be moved out of the way as needed while still under the sterile drapes. The surgical leg positioning device moves in three planes of motion: rotating, in/out, and up/down.

The present invention also provides methods for manipulating the surgical leg positioning device that may be moved in three different planes, before and during an operation.

Referring now to the drawings, where like elements are designated by like reference numerals, FIGS. 1-17 illustrate exemplary surgical leg positioning device 100 (positioning and stabilizing assembly 100) of the present invention and methods of manipulating such device during a surgical procedure, and according to exemplary embodiments of the present invention.

Surgical leg positioning device 100 is a surgical leg positioning and stabilizing device that includes a post 10 rigidly connected to a main body 50. Main body 50 is formed of a main base or plate 60 that supports a rotational positioning base or plate 70, which in turn supports a frame 80 that contacts patient's limb and provides adequate and optimized position for efficient surgical operation. As detailed below, the frame 80 includes a first curved member 81 configured to prevent a patient's leg from shifting vertically or laterally over the post, a second curved member 82, and a frame base 83 that allows sliding of the frame relative to the base 60 and the rotational positioning base 70. A sterile pad 87 is affixed to the first curved member 81. Frame 80 has a general arcuate, triangular configuration.

Surgical leg positioning device 100 also comprises a plurality of actuating mechanisms that aid in the positioning of the assembly in three planes of motion. In an exemplary-only embodiment, a first actuating mechanism 15 is provided as a pull knob 15 that raises and lowers the post 10 and, thus, main body 50 of the assembly 100 in a vertical plane (up/down direction); a second actuating mechanism 85 is provided as a lateral positioning button 85 to move the frame 80 and, thus, main body 50 of the assembly 100 laterally (in/out direction); and a third actuating mechanism 65 is provided as a rotational button 65 that rotates or pivots main body 50 of the assembly 100.

The device, designated generally by the reference numeral 100, is shown mounted in a rail adapter 20, for example, a Clark-type accessory clamp coupled to a conventional Clark rail 21 of an operating table 22.

The surgical leg positioning device 100 has mounting post 10 with a terminal pin which allows the post 10 to be raised or lowered in the rail adapter 20. Rail adapter 20 allows the post 10 and pin to move axially about a substantially vertical axis. This adjustment can be effected prior to tightening the accessory clamp by a manual tightening knob 16 which locks the post and supported components in a desired position. Knob 16 may have a scalloped configuration, for ease of manipulation. Knob 16 allows the rail adapter 20 to slide along the operating room bed rail 21 until in the desired position and then tightened to secure the rail adapter 20 in position.

The rail adapter 20 also includes a height adjustment knob 15 which is preferably round and configured to allow the vertical position of the surgical leg positioning device 100 to be adjusted as needed. An adapter post hole 23 is configured to receive post 10 of the surgical leg positioning device 100.

The post 10 is rigidly connected to main base (plate) 60 which positions and supports in cantilever fashion rotational positioning base (plate) 70. The base plate 60 is connected to the positioning plate 70 by a swivel lock (not shown) which when loosened by manual operation of rotational button 65, allows the rotational positioning base 70 to articulate with respect to the base plate 60 and to pivot or rotate the main body 50, including frame 80.

Figure 2:
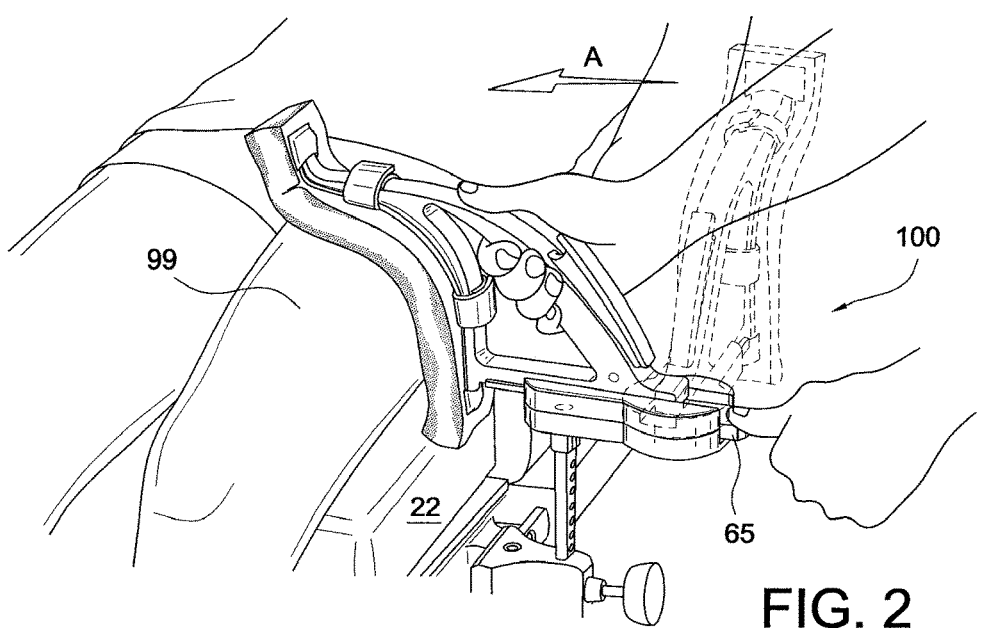
FIG. 2 illustrates the surgical leg positioning device of FIG. 1 moving in a first plane, i.e., pivoting (rotating in the direction of arrow A)
Figure 3:
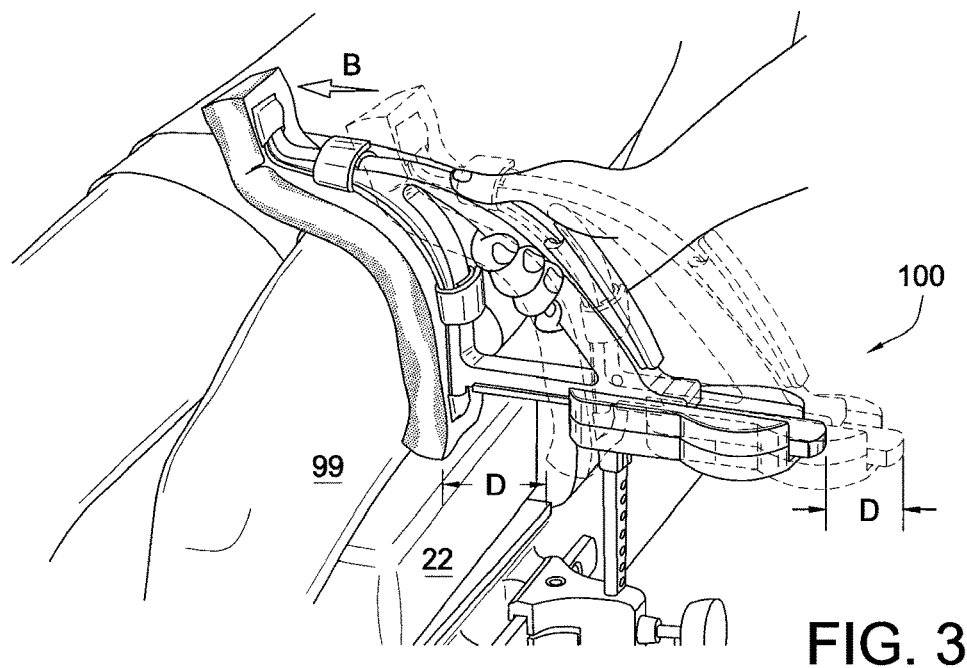
FIG. 3 illustrates the surgical leg positioning device of FIG. 1 moving in a second plane, i.e., in/out (laterally in the direction of arrow B)
Figure 4:
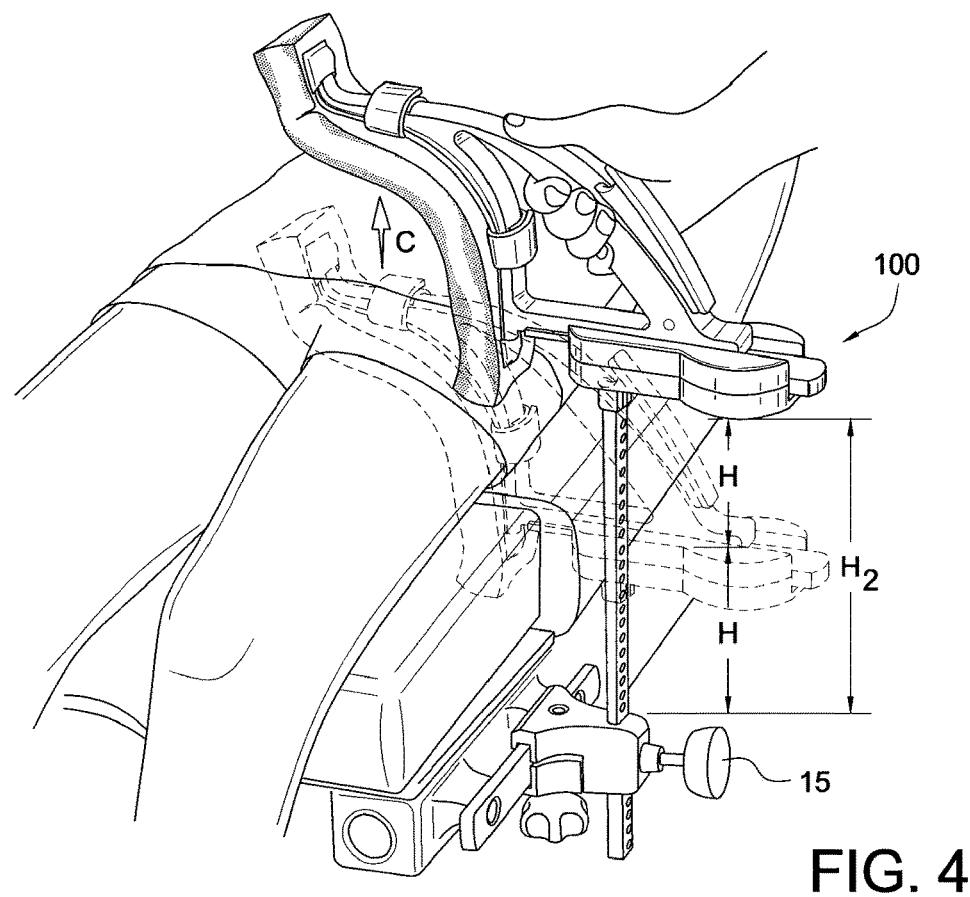
FIG. 4 illustrates the surgical leg positioning device of FIG. 1 moving in a third plane, i.e., up/down (vertically in the direction of arrow C)
Figure 5:
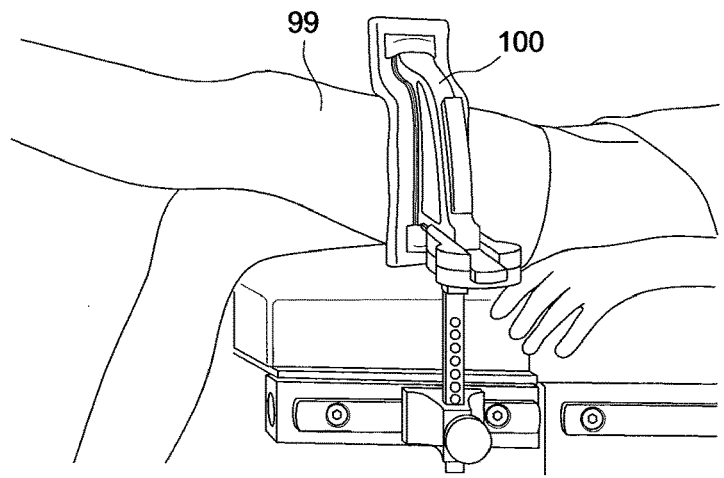
FIG. 5 illustrates the surgical leg positioning device of FIG. 1 restraining a patient's leg in position for an operation, and showing how the unique over-the-top sweeping design prevents the patient's leg from moving over the post when valgus stress or a figure four is applied.

FIGS. 2-4 illustrate the movement of the surgical leg positioning device 100 of the present invention in three planes: pivoting (rotation) in FIG. 2 (in the direction of arrow A); in/out or laterally with respect to limb 99 in FIG. 3 (in the direction of arrow B); and up/down or vertically with respect to limb 99 in FIG. 4 (in the direction of arrow C).

FIG. 2 illustrates how manually actuating or depressing button 65 causes the rotational positioning base 70 to pivot for about 90 degrees (for example, arc A') and to allow the device to pivot out of the way when the device 100 is not in use. FIG. 3 illustrates how manually actuating or depressing lateral positioning button 85 allows the frame 80 to slide for a distance D on a track on upper surface of rotational positioning base 70 (i.e., allows base member 83 of frame 80 to slide relative to the base 70, on a top surface of the base 70). FIG. 4 illustrates how manually actuating or pulling knob or button 15 allows the main body 50 to go up and down the post 10, i.e., to change from a height H1 to a height H2 (i.e., for a difference in height H).

Figure 6:
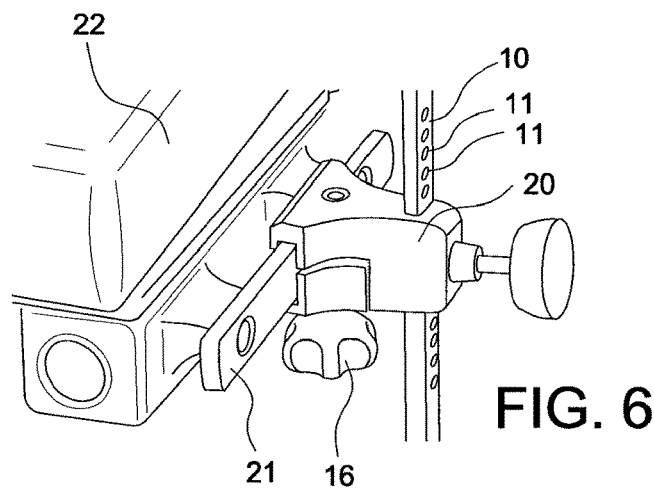
FIG. 6 is an exemplary embodiment of a rail adapter (Clark Rail adapter) of the surgical leg positioning device of the present invention, mounted on an operating room bed.

FIG. 6 illustrates details of the custom-made rail adapter 20 of the surgical leg positioning device 100 of the present invention. Post 10 is provided with a plurality of equally-spaced holes or openings 11 that allow adjusting the height of the device (relative to the rail 21, for example) by manipulating the height knob 15.

Figure 7:
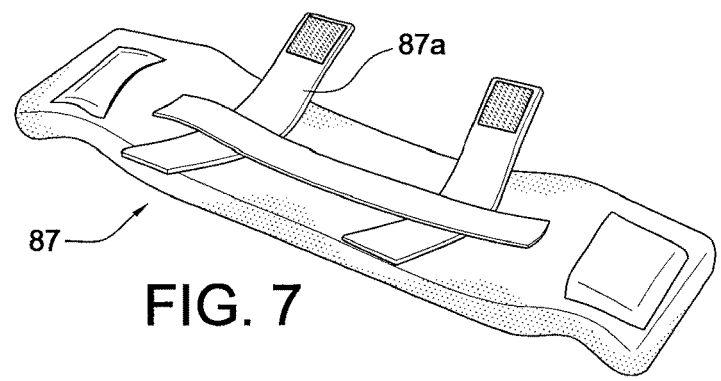
FIG. 7 is an exemplary foam pad employed with the surgical leg positioning device of the present invention.

FIG. 7 illustrates details of pad 87 that is applied on surgical leg positioning device 100 during or before the surgery. Pad 87 may be removed after use. In an exemplary embodiment, the pad 87 is a foam pad which may be disposable or reusable, sterile or non-sterile. It may be configured so as to have no specific top or bottom, and may be affixed to the surgical leg positioner by two or more pad fasteners 87a. The pad fasteners may be any suitable fastener capable of easily affixing the foam pad to the surgical leg positioner. In one example embodiment, the pad fasteners are made of double-sided Velcro®.

FIGS. 8-17 illustrate subsequent steps of utilizing the surgical leg positioning device 100 of FIG. 1 during surgery. A person of ordinary skill in the art would know that the positioning steps may be performed in any order that results in the surgical leg positioning device holding a patient's leg in an appropriate position.

Figure 8:
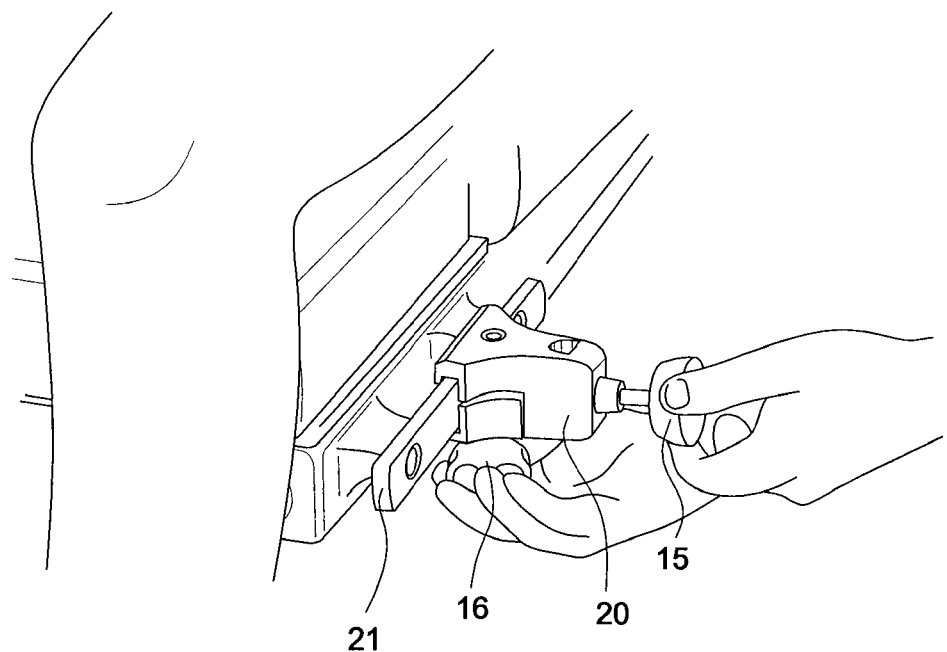
FIGS. 8-17 illustrate sequential steps of one exemplary method of using and manipulating the surgical leg positioning device of FIG. 1 during a surgical procedure.
Figure 9:
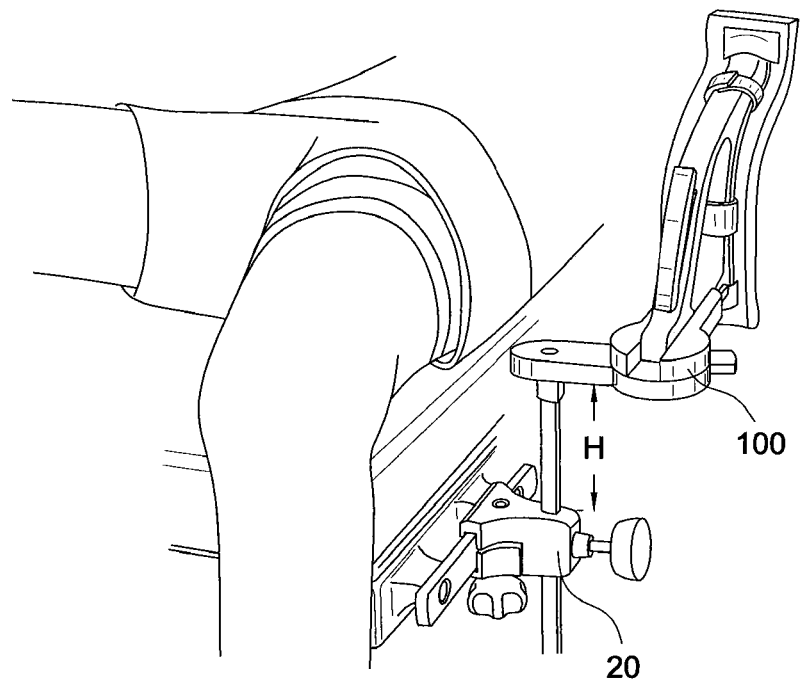
Figure 10:
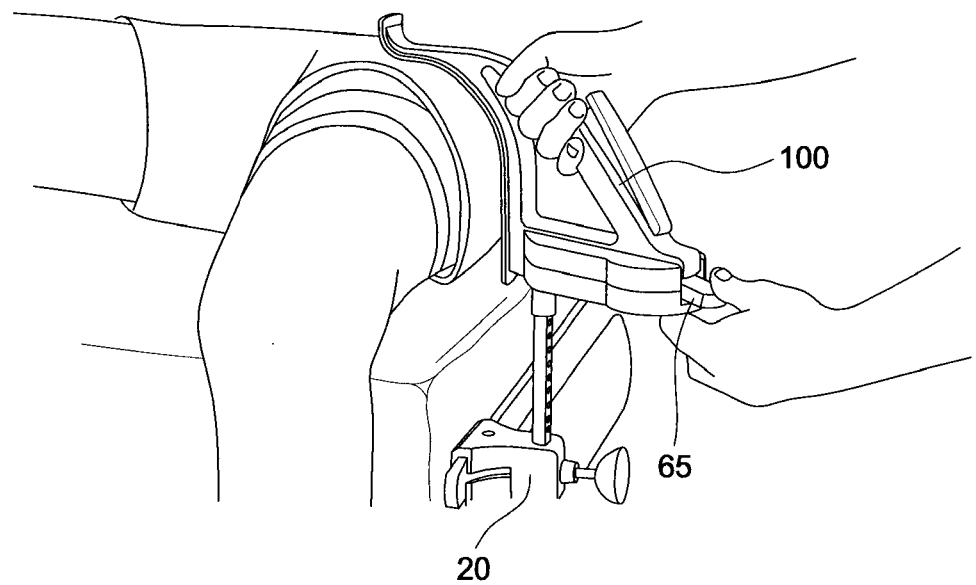
Figure 11:
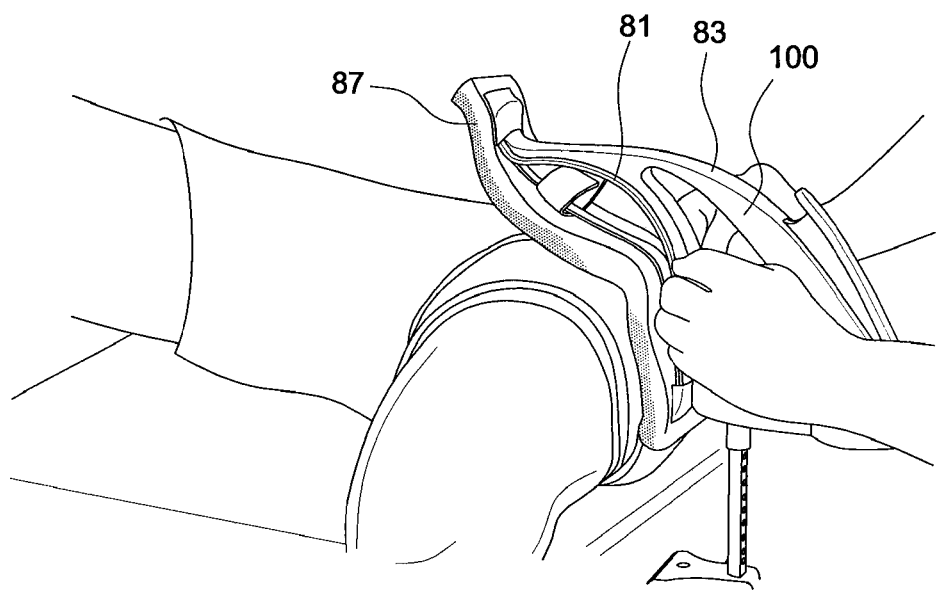
Figure 12:
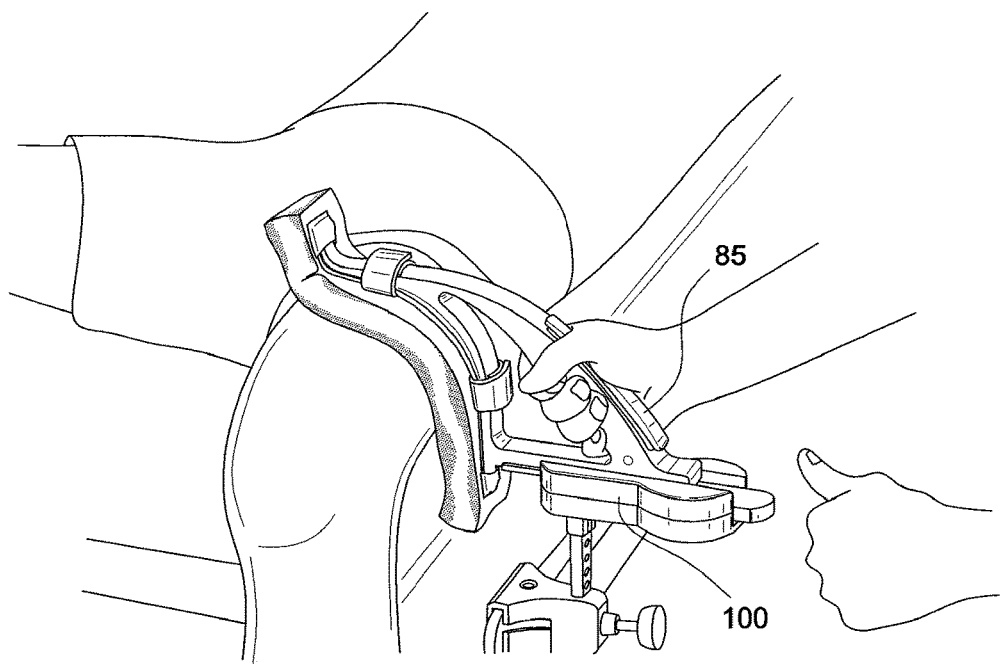
Figure 13:
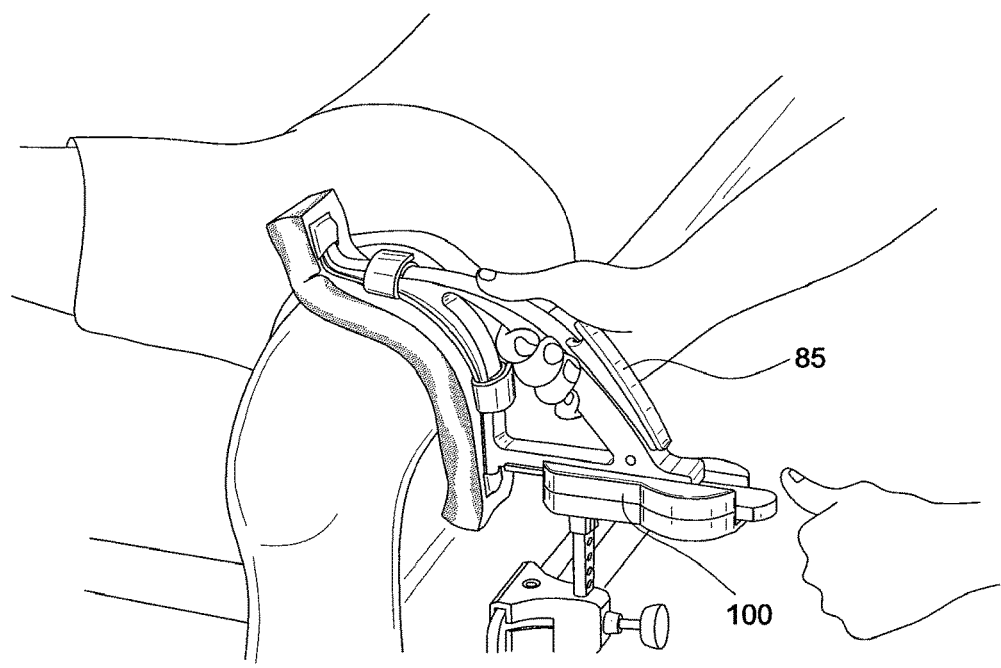
Figure 14:
Figure 15:
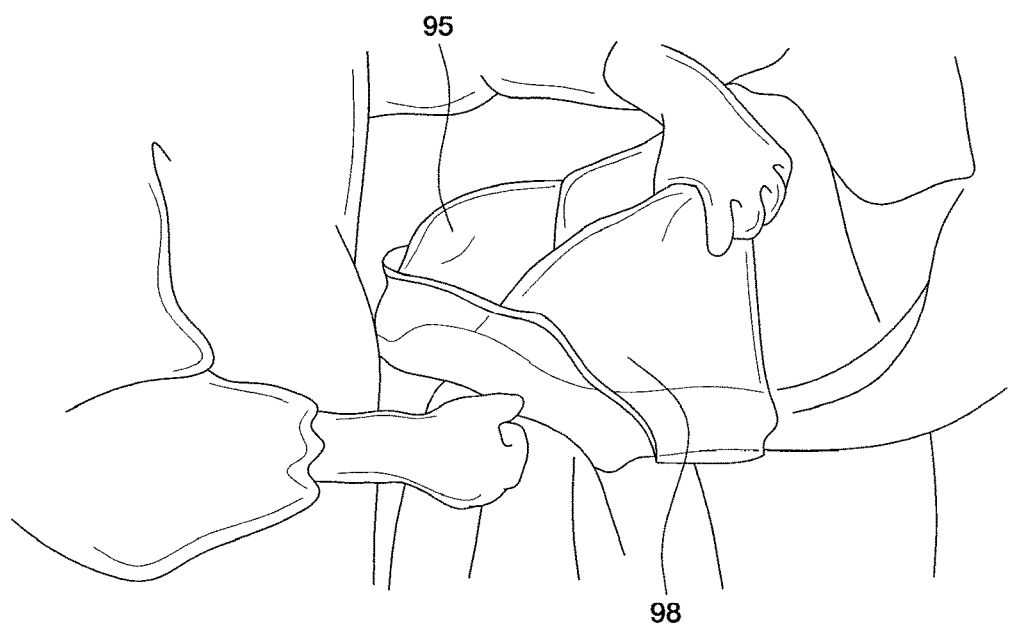
Figure 16:
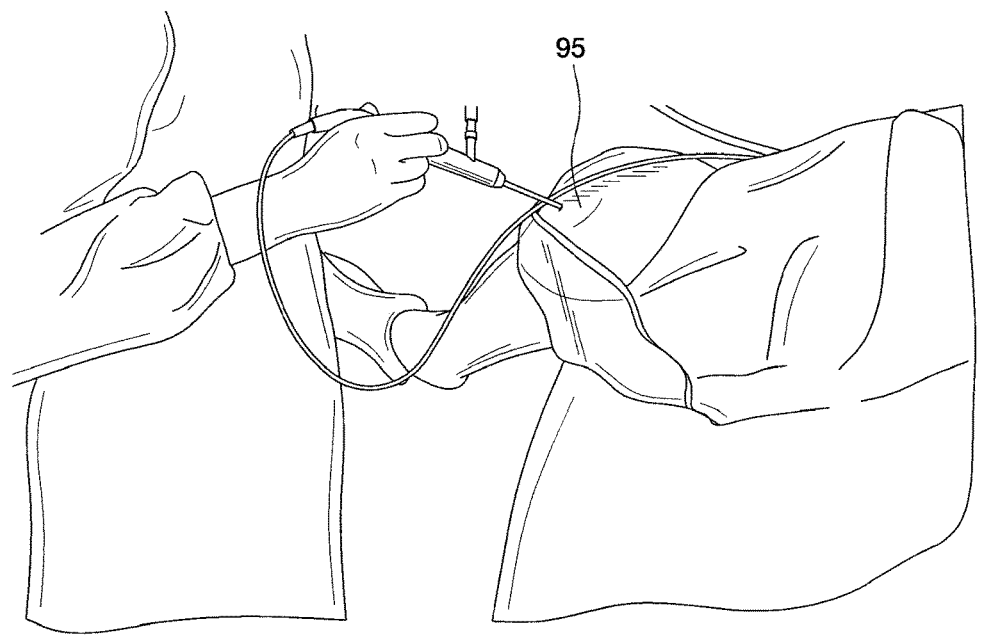
Figure 17:
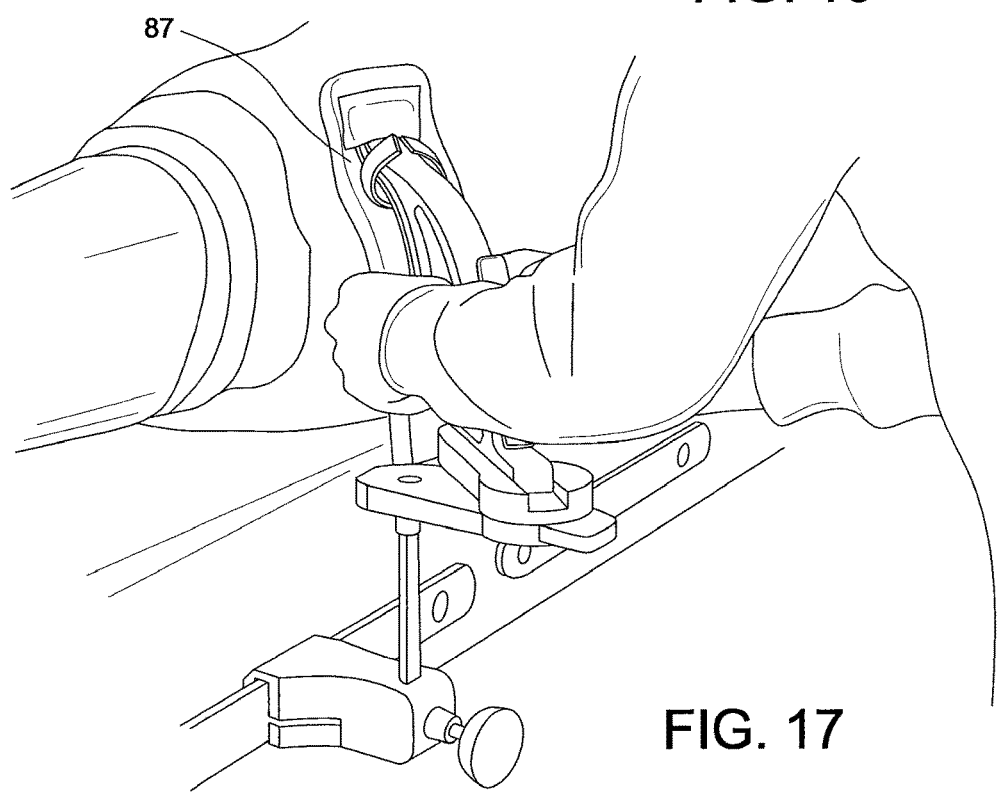

FIG. 8: placing the rail adapter 20 and tightening the Clark knob 16 (mounting the rail adapter 20 to a rail provided on an operating room bed, positioning the rail adapter 20 in a desired location, and securing the rail adapter 20 by manipulating the adapter knob 16);

FIG. 9: placing the post 10 into the rail adapter 20; adjusting height H by manipulating the height knob 15 (adjusting the surgical leg positioning device 100 to a desired height H by manipulating the height adjustment knob 15 of the adapter, after the post 10 has been placed in a receiver hole 23 of the rail adapter assembly 20);

FIG. 10: rotating/pivoting the surgical knee positioner 100 by manipulating the rotational button 65 (adjusting the rotational position of the surgical leg positioning device by manipulating the rotational button);

FIG. 11: affixing the foam pad 87 to the device; this step can occur before or after any positioning, or between any positioning steps (affixing foam pad 87 to first curved member 81);

FIG. 12: laterally positioning the device 100 by manipulating the lateral positioning button 85 (adjusting the lateral position of the surgical leg positioning device 100 by manipulating the lateral positioning button 85);

FIG. 13: surgical knee positioner 100 is in desired position (the surgical leg positioning device 100 in a desired location for an operation);

FIG. 14: patient's leg 99 and surgical knee positioner 100 are fully covered in sterile surgical drapes 98 (the surgical leg positioning device 100 and patient's leg 99 are covered in sterile surgical drapes 98 during an operation);

FIG. 15: move the surgical leg positioning device 100 out of the way without removing sterile surgical drapes 98 (moving the surgical leg positioning device 100 along at least one plane of motion without removing the sterile surgical drape 98);

FIG. 16: surgical knee positioner 100 no longer in the way (depicts the operation continuing on knee 95 after the surgical leg positioning device 100 has been moved after it was no longer needed);

FIG. 17: removing the pad 87 after surgery is finished (after completion of the operation, for example, arthroscopic knee surgery).

The exemplary surgical leg positioning device 100 may be provided as part of a kit that includes a custom made rail adapter 20 to be attached to a rail, a post 10 attached to main body 50, and at least one foam pad 87, preferably disposable. In a specific exemplary embodiment, the kit may include five non-sterile disposable pads, with no specific top and bottom, and with double-sided Velcro®.

The novel device 100 of the present invention provides the following benefits and features:
- Prevents patient's leg from moving over post when valgus stress is applied
- Three planes of motion (rotation, in/out, up/down)
- Small compact size allows surgeons to operate around easily the surgical drape
- Minimal weight and simple set-up for OR staff
- Disposable pad that is easy to put on and take off
- Ergonomic, oversized buttons are easily located under the drape and easy to access A leg positioning assembly 100 of the present invention comprises: a post 10; and a main body 50 including a main base or plate 60 rigidly connected to the post 10, a rotational positioning base 70 supported by the main base or plate 60, a frame 80 supported by the rotational positioning base 70 and configured to slide relative to the rotational positioning base, and three actuating mechanisms 15, 65, 85 that allow the main body 50 to move in three different planes of motion without removing sterile surgical drapes 98 around the leg 99 and knee 95 during the surgery.

The three actuating mechanisms include a first actuating mechanism in the form of a pull knob 15 attached to a rail adapter 20 to raise and lower the post 10 attached to the main body 50 relative to the rail adapter and in a vertical plane; a second actuating mechanism in the form of a lateral positioning button 85 to move the frame 80 laterally relative to the leg 99 and in a horizontal plane; and a third actuating mechanism in the form of a rotational button 65 to pivot or rotate the main body 50 in a rotational plane.

A method of conducting arthroscopic surgery with device 100 of the present invention comprises inter alia the steps of: (i) positioning the surgical leg positioning device 100 in a desired location relative to the patient's leg 99; (ii) draping a sterile surgical drape 98 over the patient's leg and the surgical leg positioning device 100; and (iii) moving the surgical leg positioning device 100 along three different planes of motion without removing at all times the sterile surgical drape 98.

The method may further comprise the steps of: mounting rail adapter 20 to a rail attached to an operating room bed; positioning the rail adapter 20 in a desired location and securing the rail adapter by manipulating an adapter knob 16; placing the post 10 in a receiver hole of the rail adapter 20; adjusting the surgical leg positioning device to a desired height H by manipulating a height adjustment knob 15 of the rail adapter 20; adjusting a rotational position of the surgical leg positioning device 100 by manipulating a rotational button 65 on the main body 50; and adjusting a lateral position of the surgical leg positioning device 100 by manipulating a lateral positioning button 85.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed as new and desired to be protected by Letters Patent of the United States is:

1. A surgical leg positioning device for stabilizing a patient's limb during surgery, comprising:
   a rail adapter;
   a mounting post slidably received within a post hole of the rail adapter;
   a main base rigidly connected to the mounting post;
   a positioning base supported by the main base and configured to rotate relative to the main base;
   a frame slidably supported by the positioning base,
   wherein a frame base of the frame is received within a track formed in the positioning base,
   wherein a floor of the track is recessed below an uppermost surface of the positioning base such that at least a portion of the frame base is positioned below the uppermost surface;
   a sterile pad affixed to a first curved member of the frame;
   a manual tightening knob that is actuable to allow the rail adapter to slide along a rail of an operating table;
   a pull knob that is actuable to raise and lower the mounting post relative to the rail adapter;
   a lateral positioning button that is downwardly depressible into a recess formed in a second curved member of the frame to slide the frame base relative to the positioning base,
   wherein the first curved member and the second curved member are directly connected to and extend upwardly from different locations of the frame base and meet together at another location that is vertically offset from the frame base; and
   a rotational button mounted within a recess of the main base and that is actuable to rotate the positioning base relative to the main base such that, in use, the sterile pad is movable in an over-the-top rotational sweeping motion relative to the patient's limb as the positioning base rotates relative to the main base.

2. The surgical leg positioning device of claim 1, wherein the first curved member is configured to prevent the patient's limb from shifting vertically or laterally over the mounting post.

3. The surgical leg positioning device of claim 1, wherein the rail adapter is configured for coupling to a rail of the operating table, the rail adapter further being configured to allow the mounting post to slide within the post hole of the rail adapter and to be securely locked to the rail adapter by manually tightening the manually tightening knob.

4. A method of using the surgical leg positioning device of claim 1, during an operation, comprising the steps of:
   positioning the surgical leg positioning device in a desired location relative to the patient's limb;
   draping a sterile surgical drape over the patient's limb and the surgical leg positioning device; and
   moving the surgical leg positioning device along three different planes of motion without removing the sterile surgical drape.

5. The method of claim 4, further comprising the steps of:
   mounting the rail adapter to a rail attached to the operating table;
   positioning the rail adapter in a desired location and securing the rail adapter by manipulating the manually tightening knob;
   placing the mounting post in the post hole of the rail adapter;
   adjusting the surgical leg positioning device to a desired height by manipulating the pull knob;
   adjusting a rotational position of the surgical leg positioning device by manipulating the rotational button; and
   adjusting a lateral position of the surgical leg positioning device by manipulating the lateral positioning button.

6. The method of claim 4, wherein the operation is an arthroscopic knee surgery.

7. The surgical leg positioning device of claim 1, wherein the frame includes an arcuate, triangular configuration.

8. The surgical leg positioning device of claim 1, wherein the first curved member and the second curved member meet together at an upper corner of the frame.

9. The surgical leg positioning device of claim 1, wherein the sterile pad is affixed to the first curved member with a first pad fastener and is affixed to the second curved member with a second pad fastener.

10. The surgical leg positioning device of claim 9, wherein the first pad fastener and the second pad fastener include double-sided hook and loop material.

11. The surgical leg positioning device of claim 1, comprising a triangular opening established between the frame base, the first curved member, and the second curved member.

12. The surgical leg positioning device of claim 1, wherein the sterile pad is movable at least 90 degrees during the over-the-top rotational sweeping motion.

* * * * *